US005545748A

United States Patent [19]

Rowland et al.

[11] Patent Number: 5,545,748

[45] Date of Patent: Aug. 13, 1996

[54] POLYGLYCOLATE PERACID PRECURSORS

[75] Inventors: Richard R. Rowland, Danville; Ronald A. Fong, Modesto; Richard J. Wiersema, Tracy; Alfred G. Zielske, Pleasanton, all of Calif.

[73] Assignee: The Clorox Company, Oakland, Calif.

[21] Appl. No.: 325,050

[22] Filed: Oct. 18, 1994

Related U.S. Application Data

[62] Division of Ser. No. 951,238, Sep. 25, 1992, Pat. No. 5,391,812, which is a division of Ser. No. 329,982, Mar. 29, 1989, Pat. No. 5,182,045.

[51] Int. Cl.[6] .......................... C07C 409/02; C01B 15/10

[52] U.S. Cl. .................... 562/2; 252/186.26; 252/186.42

[58] Field of Search .......................... 562/2; 252/186.26, 252/186.42

[56] References Cited

U.S. PATENT DOCUMENTS

| | | | |
|---|---|---|---|
| 3,130,165 | 4/1964 | Brocklehurst | 252/99 |
| 3,960,743 | 6/1976 | Nakagawa et al. | 252/99 |
| 3,996,152 | 12/1976 | Edwards et al. | 252/186.42 |
| 4,283,301 | 8/1981 | Diehl | 252/102 |
| 4,337,213 | 6/1982 | Marynowski et al. | 568/566 |
| 4,367,156 | 1/1983 | Diehl | 252/102 |
| 4,412,934 | 11/1983 | Chung et al. | 252/186.38 |
| 4,483,778 | 11/1984 | Thompson et al. | 252/94 |
| 4,486,327 | 12/1984 | Murphy et al. | 252/94 |
| 4,536,314 | 8/1985 | Hardy et al. | 252/102 |
| 4,539,130 | 9/1985 | Thompson et al. | 252/94 |

(List continued on next page.)

FOREIGN PATENT DOCUMENTS

| | | |
|---|---|---|
| 0079745A1 | of 1982 | European Pat. Off. . |
| 0124262A2 | of 1984 | European Pat. Off. . |
| 2175621 | of 1986 | United Kingdom . |

OTHER PUBLICATIONS

Anson et al., "Highly Stabilized Copper(III) Complexes," *J. Am. Chem. Soc.*, 109: 10, (Apr. 1987), pp. 2974–2979.

Greene, Theodora W., *Protective Groups in Organic Synthesis*, New York: John Wiley & Sons, p. 183, (Mar. 1983).

Koshy et al., "Partial Synthesis and Physical Properties of Cerebroside Sulfate Containing Palmitic Acid or (List continued on next page.)

*Primary Examiner*—Sharon A. Gibson
*Assistant Examiner*—Joseph D. Anthony
*Attorney, Agent, or Firm*—Majestic, Parsons, Siebert & Hsue

[57] ABSTRACT

Polyglycolate compounds are provided having the general structure:

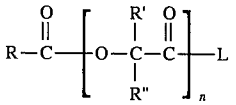

wherein n is an integer from 2 to about 10; R is $C_{1-20}$ linear or branched alkyl, alkoxylated alkyl, cycloalkyl, aryl, alkylaryl, substituted aryl; R' and R" are independently H, $C_{1-20}$ alkyl, aryl, $C_{1-20}$ alkylaryl, substituted aryl, and $NR_3^{\alpha+}$, wherein $R^{\alpha}$ is $C_{1-30}$ alkyl; and L is a leaving group displaceable in a peroxygen bleaching solution by perhydroxide anion. When this compound is combined with a source of peroxgen in aqueous solution, then a plurality of stain removing peracids are formed. Such peracids are formed substantially sequentially beginning with the carbonyl adjacent to the leaving group L. Thus, a first stain removing peracid having the structure

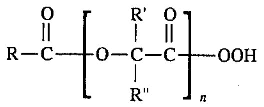

will be formed in amounts approaching quantitative yield.

2 Claims, 5 Drawing Sheets

U.S. PATENT DOCUMENTS

| | | | |
|---|---|---|---|
| 4,681,592 | 7/1987 | Hardy et al. | 8/111 |
| 4,735,740 | 4/1988 | Zielske | 252/95 |
| 4,778,618 | 10/1988 | Fong et al. | 252/186.23 |
| 4,916,230 | 4/1990 | Alexander | 546/318 |
| 4,957,647 | 9/1990 | Zielske | 252/186.38 |
| 4,985,180 | 1/1991 | Bellis et al. | 560/17 |
| 5,087,385 | 2/1992 | Zielske | 252/186.39 |
| 5,124,475 | 6/1992 | Nepras et al. | 554/90 |
| 5,182,045 | 1/1993 | Rowland et al. | 252/186.38 |

OTHER PUBLICATIONS

α–Hydroxy Palmitic Acid," *Chemistry and Physics of Lipids*, 34, (May 1983), pp. 41–53.

White et al., "Stereochemical Dynamics of Aliphatic Hydroxylation by Cytochroms P–450," *J. Am. Chem. Soc.*, 108, (Feb. 1986), pp. 6024–6031.

POLYGLYCOLATE PERACID PRECURSORS

This is a division of application Ser. No. 07/951,238, filed Sep. 25, 1992, now U.S. Pat. No. 5,391,812, which was a divisional of prior application Ser. No. 07/329,982, filed Mar. 29, 1989, and now issued as U.S. Pat. No. 5,182,045, issued Jan. 26, 1993.

TECHNICAL FIELD

This invention generally relates to peracid bleaching, and more particularly to peracid precursors having the general formula

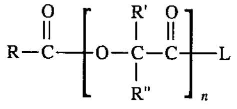

where n is 2 to about 10 and L is a leaving group that is displaced in a peroxygen bleaching solution by perhydroxide anion.

BACKGROUND OF THE INVENTION

Peroxy compounds are effective bleaching agents, and compositions including mono- or diperoxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid presents a problem of storage stability for compositions consisting of or including peroxyacids.

One approach to the problem of reduced bleaching activity of peroxyacid compositions has been to include "activators" for or precursors of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester. However, these bleach activators tend to yield an unpleasant odor under actual wash conditions. U.S. Pat. No. 4,486,327, inventors Murphy et al., issued Dec. 4, 1984, and U.S. Pat. No. 4,536,314, inventors Hardy et al., issued Aug. 20, 1985, disclose certain alpha substituted derivatives of $C_6$–$C_{18}$ carboxylic acids which are said to activate peroxygen bleaches and are Said to reduce malodor.

U.S. Pat. No. 4,539,130, inventors Thompson et al., issued Sep. 3, 1985 (and its related U.S. Pat. No. 4,483,778, inventors Thompson et al., issued Nov. 20, 1984) disclose chloro, methoxy or ethoxy substituted on the carbon adjacent to the acyl carbon atom. U.S. Pat. No. 3,130,165, inventor Brocklehurst, issued Apr. 21, 1964, also discloses an α-chlorinated peroxyacid, which is said to be highly reactive and unstable.

U. S. Pat. No. 4,681,952, inventors Hardy et al., issued Jul. 21, 1987, discloses peracids and peracid precursors said to be of the general type RXAOOH and RXAL, wherein R is said to be a hydrocarbyl group, X is said to be a hetero-atom, A is said to be a carbonyl bridging group, and L is a leaving group, such as an oxybenzene sulfonate. $C_6$ through $C_{20}$ alkyl substituted aryl are said to be preferred as R, with $C_6$–$C_{15}$ alkyl said to be especially preferred for oxidative stability.

Chung et al., U.S. Pat. No. 4,412,934, issued Nov. 1, 1983, discloses bleaching compositions containing a peroxygen bleaching compound and a bleach activator of the general formula

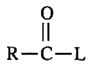

wherein R is an alkyl group containing from about 5 to about 18 carbon atoms, and L is a leaving group, the conjugate acid of which has a $pK_\alpha$ in the range of about 6 to about 13.

Nakagawa et al., U.S. Pat. No. 3,960,743, issued Jun. 1, 1976, discloses an activating agent represented by the formula

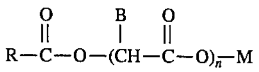

wherein R stands for an alkyl group having 1 to 15 carbon atoms, a halogen- or hydroxyl-substituted alkyl group having 1 to 16 carbon atoms or a substituted aryl group, B designates a hydrogen atom or an alkyl group having 1 to 3 carbon atoms, M represents a hydrogen atom, an alkyl group having 1 to 4 carbon atoms or an alkali metal, and n is an integer of at least 1 when M is an alkyl group or n is an integer of at least 2 when M is a hydrogen atom or an alkali metal. However, perhydrolysis of this activating agent substantially does not occur at the carbonyl adjacent the M substituent and the overall perhydrolysis that does occur tends to occur relatively slowly.

U.S. Pat. No. 4,778,618, Fong et al., issued Oct. 18, 1988 provides novel bleaching compositions comprising peracid precursors with the general structure

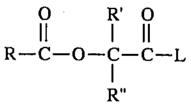

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_3^{\alpha+}$, wherein $R^\alpha$ is $C_{1-30}$ alkyl; and where L is a leaving group which can be displaced in a peroxygen bleaching solution by perhydroxide anion. The present invention is related to the Fong et al. glycolate ester peracid precursors in that precursors of the present invention are polyglycolates of the Fong et al. monoglycolate precursors. Further, compositions of the invention preferably include admixtures of the polyglycolate and glycolate precursors.

SUMMARY OF THE INVENTION

In one aspect of the present invention, a bleaching composition comprises a peracid precursor having the general structure:

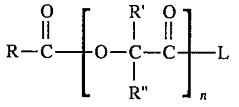

wherein n is 2 to about 10; R is $C_1$–$C_{20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_3^{\alpha+}$, wherein $R^\alpha$ is $C_{1-30}$ alkyl, more preferably where one of R' and R" is methyl or H and the other is H; and L is a leaving group displaceable in a peroxygen bleaching solution by perhydroxide anion. When this peracid precursor is combined with a source of peroxygen in aqueous solution, then a plurality of stain removing peracids are formed. Such peracids are formed substantially sequentially beginning with the carbonyl adjacent to the leaving group L. Thus, when a peracid precursor is dissolved in aqueous solution and is in the presence of sufficient peroxygen source, then a first stain removing peracid having the structure

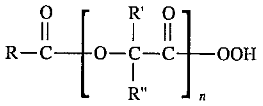

will be formed in amounts approaching quantitative yield. Subsequent stain removing peracids then form in solution so that there is a high level of bleaching capacity maintained over a typical wash cycle.

In another aspect of the present invention, the just described peracid precursor is admixed with a monoglycolate peracid precursor having substantially the same general structure, but wherein n is 1. This admixture provides a mixture of soluble peracids and surface active peracids during the wash cycle. Soluble peracids are believed to assist in reducing dye transfer. Commercial preparation of the admixture is also easier and less expensive than preparing either substantially pure monoglycolate peracid precursor or peracid precursor that is substantially entirely polyglycolate.

DETAILED DESCRIPTION OF PREFERRED EMBODIMENTS

Compounds of the invention are peracid precursors having the general structure:

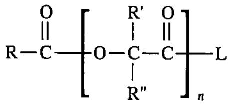

wherein n is 2 to about 10, preferably an average of about 4; R is $C_1$–$C_{20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $NR_3^{\alpha+}$, wherein $R^\alpha$ is $C_{1-30}$ alkyl, preferably where one of R' and R" is methyl or H and the other is H; and L is a leaving group displaceable in a peroxygen bleaching solution by perhydroxide anion.

When this peracid precursor is combined with a source of peroxygen in aqueous solution, then a plurality of stain removing peracids are formed. Such peracids are formed substantially sequentially down the carbon chain at the carbonyls, beginning with the carbonyl adjacent to the leaving group L. Thus, when a peracid precursor is dissolved in aqueous solution and is in the presence of sufficient peroxygen source, then a first stain removing peracid having the structure

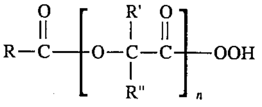

will be formed in amounts approaching quantitative yield. Subsequent stain removing peracids then form in solution so that there is a high level of bleaching capacity maintained over a typical wash cycle. Among the peracids formed are both soluble and surface active peracids. Soluble peracids are believed to assist in preventing dye transfer during laundering of colored fabrics.

A particularly preferred peracid precursor and the "cascade" of bleaching compounds formed in aqueous solution in the presence of perhydroxide anions therefrom, are illustrated by Reaction Scheme I.

REACTION SCHEME I

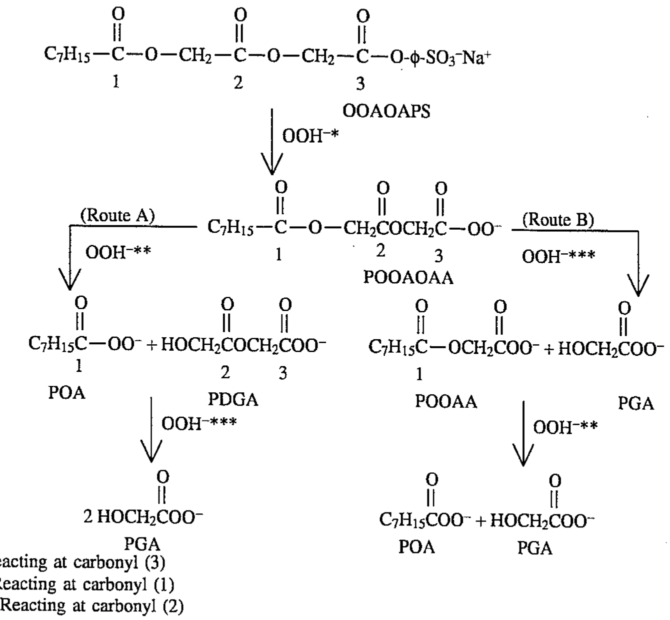

OOAOAPS

POOAOAA

POA PDGA POOAA PGA

PGA POA PGA

*Reacting at carbonyl (3)
**Reacting at carbonyl (1)
***Reacting at carbonyl (2)

Figure 1:
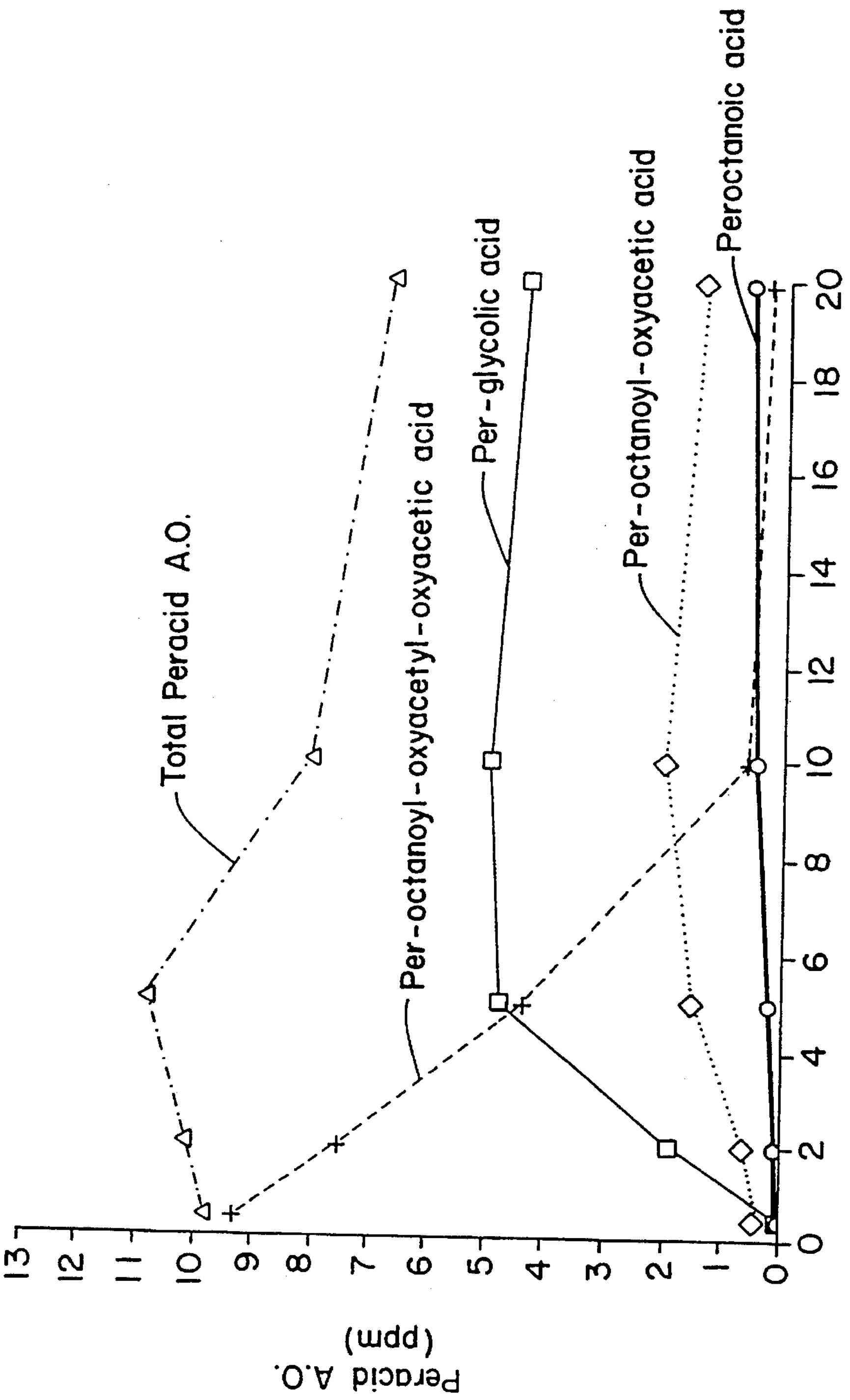
FIG. 1 graphically illustrates the speciation of peracids in a solution over time where 0.8 mM of a precursor embodiment of the invention (sodium-p-(n-octanoyl-di-[oxyacetyl]-oxy)-benzene sulfonate) was dissolved in the presence of hydrogen peroxide at pH 10.0 and at a hydrogen peroxide to precursor mole ratio of 2:1.

As illustrated by Reaction Scheme I, the peracid precursor designated OOAOAPS (where R=$C_7$, R' and R" are H, L is —O—Ø—$SO_3Na$ and n=2) can give almost quantitative production of the first peracid in the cascade. This first peracid is designated POOAOAA and provides stain removal. Proceeding down the cascade (Route B), another good stain removing peracid is formed. This second peracid is designated POOAA. In yet another stage of the cascade, the peracid designated POA (i.e., peroctanoic acid) is formed, which is a stain removing peracid. These sequentially formed peracids together maintain a high level of total peracid available for bleaching over a twenty minute period, as is illustrated by FIG. 1 (where the initial OOAOAPS compound and peroxide were in a 1:2 molar ratio and the species were monitored at room temperature by HPLC with an iodometric detector). The peracid designated PGA is water soluble while the POOAA and POA are surface active peracids. Reaction Scheme I indicates that minor amounts of the compound PDGA are probably formed, along with POA, and then to PGA.

As may be seen from Reaction Scheme I, the peracid precursor has n=2. Where the polyglycolates are in a mixture, for example so that the average of n is 4, then the reactions are much more complicated than shown by Reaction Scheme I since there are many more reactive sites and the "cascade" formation of peracids appears to occur even more rapidly. Table I illustrates the species formed where R=$C_7$, R' and R" are H, L is —O—Ø—$SO_3Na$ and n is an average of 4 (hydrogen peroxide being the limiting reagent). The pH was 10.5, temperature was 23° C., precursor was in 1:2 molar ratio with respect to $H_2O_2$, and the initial precursor concentration was 0.8 mM.

TABLE I

| | Peracid Species[1] (mM) | | | | | |
|---|---|---|---|---|---|---|
| Elasped Time (min) | Per-glycolic[2] | n = 0 | n = 1 | n = 2 | n = 3 | n = 4 |
| 2 | 0.640 | 0.017 | 0.126 | 0.076 | 0.015 | 0.004 |

TABLE I-continued

| | Peracid Species[1] (mM) | | | | | |
|---|---|---|---|---|---|---|
| Elasped Time (min) | Per-glycolic[2] | n = 0 | n = 1 | n = 2 | n = 3 | n = 4 |
| 5 | 0.724 | 0.020 | 0.156 | 0.027 | 0.001 | — |
| 10 | 0.589 | 0.053 | 0.130 | 0.031 | — | — |

Figure 2:
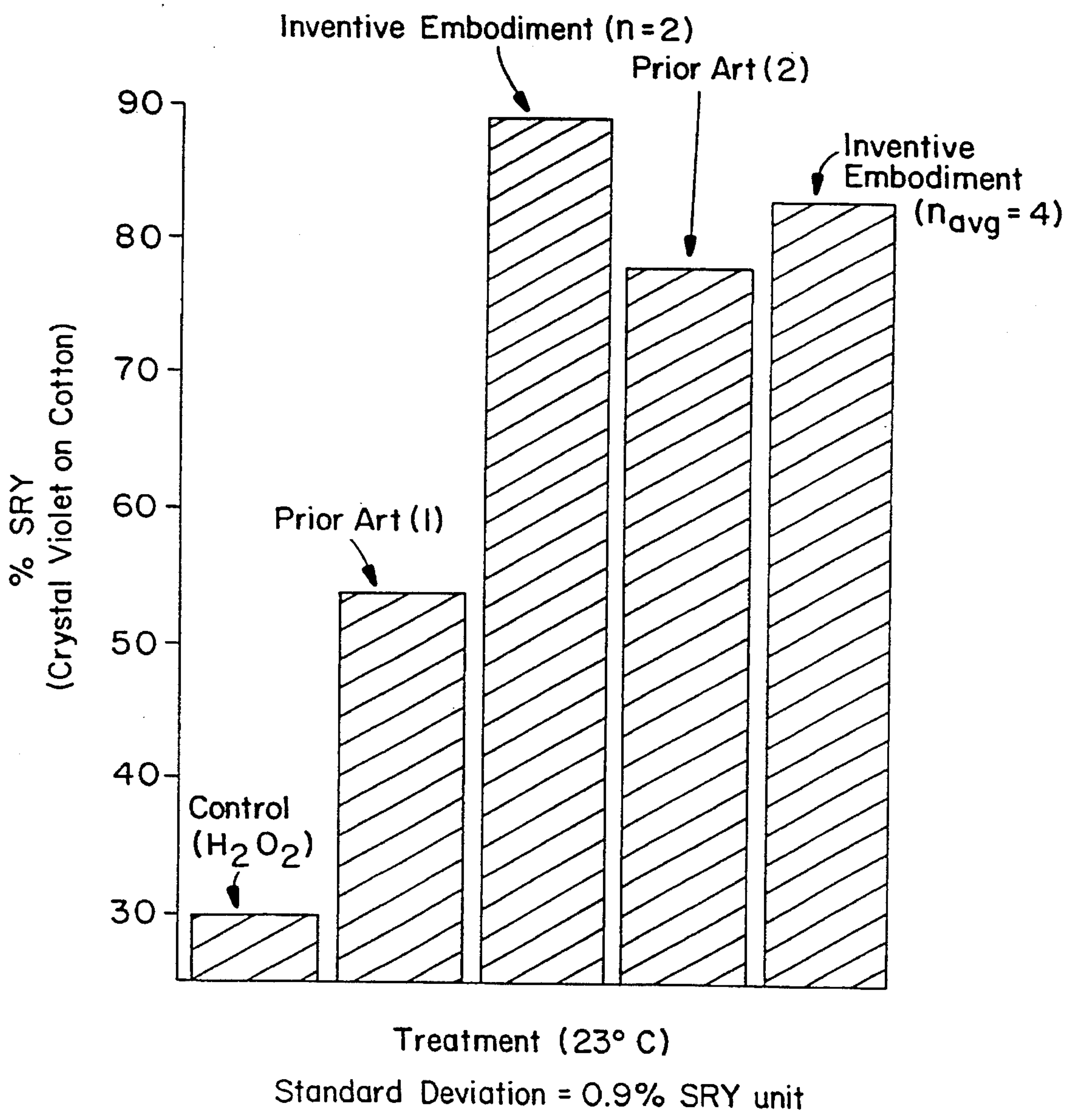
FIG. 2 graphically illustrates the percent stain removal of crystal violet on cotton at 23° C. from use of two precursor embodiments of the invention (14 ppm theoretical A.O.), and from use of two prior art compounds (prior art (1) and (2)) for comparison (14 ppm theoretical A.O.), as well as from use of hydrogen peroxide (28 ppm A.O.) alone as a control.

[1]Having the formula 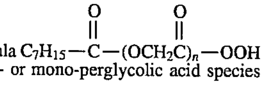
[2]The sum of poly- or mono-perglycolic acid species Turning to FIG. 2, the OOAOAPS inventive polyglycolate is shown to provide significantly better stain removal of crystal violet on cotton when dissolved as a theoretical A.O. of 14 ppm (for phenol sulfonate ester) solution with 28 ppm A.O. $H_2O_2$ present than is provided with 28 ppm hydrogen peroxide by itself at 23° C. Similarly, another inventive polyglycolate (where n averages 4) designated "OOPOAPS" also provides good stain removal. For comparison, two comparative (prior art) compounds were also tested for crystal violet stain removal on cotton at 23° C. as theoretical A.O. of 14 ppm solutions with 28 ppm A.O. $H_2O_2$ present. These two comparative compounds are designated "prior art (1)" and "prior art (2)", respectively. As can be seen from FIG. 2, both of the inventive precursors provided better stain removal than both of the comparative compounds. All solutions were tested at pH 10. These two comparative compounds had the structures shown below (disclosed by U.S. Pat. 3,960,743, supra).

COMPARATIVE STRUCTURES

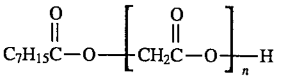

n = 2

Prior Art (1)

-continued

COMPARATIVE STRUCTURES

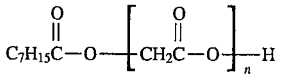

$n_{avg.} = 4$

Prior Art (2)

Figure 3:
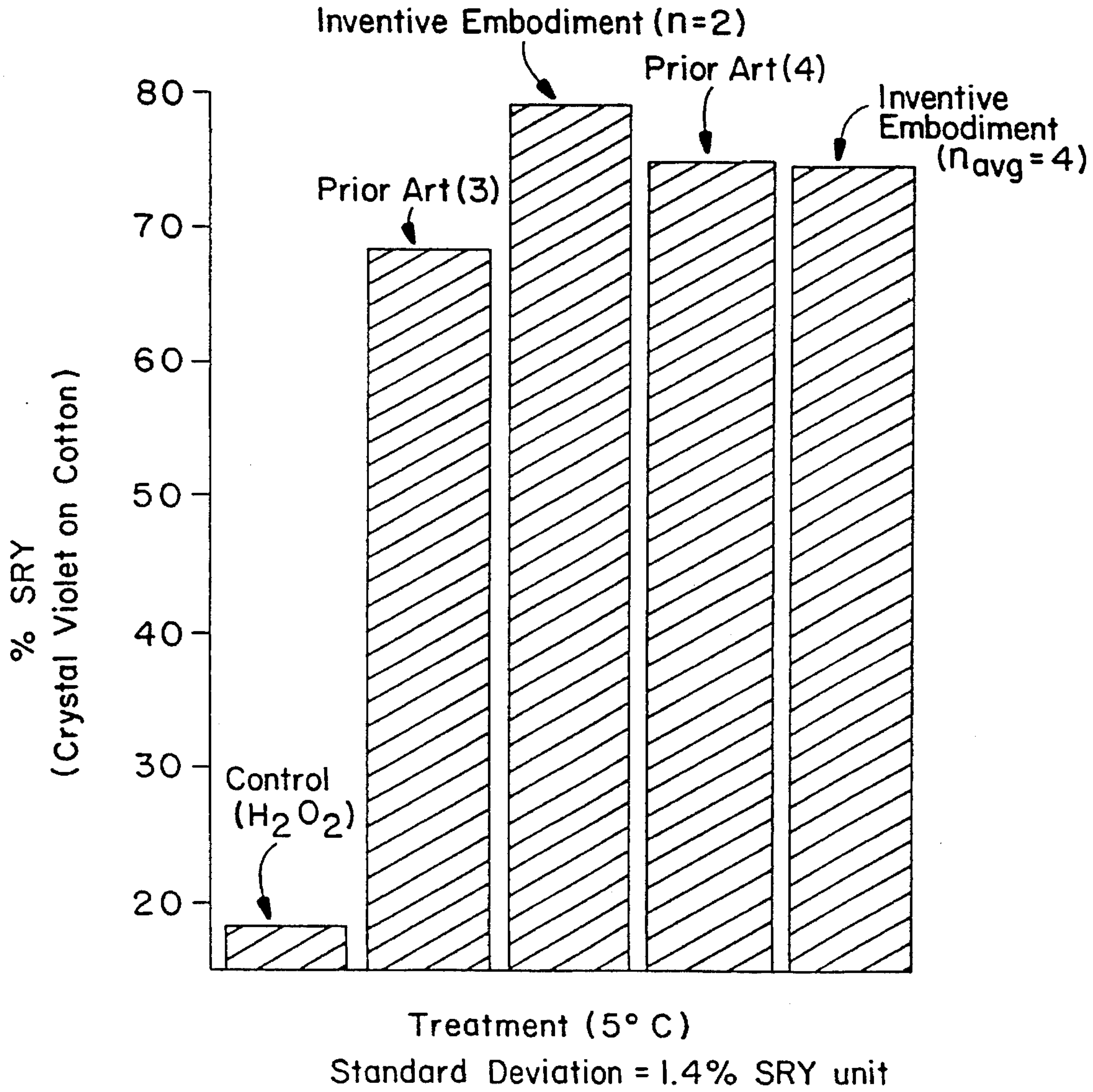
FIG. 3 graphically illustrates the percent stain removal of crystal violet on cotton at 5° C. from use of two precursor embodiments of the invention and, for comparison, from use of a third prior art composition (prior art (3)), as well as from use of hydrogen peroxide alone as a control and from use of preformed peroctanoic acid (prior art (4))

Turning to FIG. 3, the two embodiments of the invention described in connection with FIG. 2 are again shown for crystal violet stain removal, but at 5° C. Hydrogen peroxide is shown as control (at 28 ppm A.O. rather than the 14 ppm of the precursors), and another two prior art comparative compositions (designated as "prior art (3)" (disclosed by U.S. Pat. 4,412,934, supra) and "prior art (4)") having the structures shown below are shown for stain removal under the same conditions.

COMPARATIVE STRUCTURES

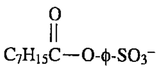

Prior Art (3)

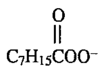

Prior Art (4)

As is seen by the above comparative structures, prior art (3) is a peracid precursor while prior art (4) is a preformed peracid. The similar stain removal performance of the inventive precursors with respect to prior art (4), that is, peroctanoic acid, or "POA", is quite surprising and means that formulations of the invention intended for use in cold or cool water washes (such as, for example, from about 5° C. to about 15° C.) should provide as good stain removal as would a peracid such as peroctanoic acid; without, however, the well-known stability and handling problems of such preformed peracids. This surprising performance in cold or cool water can be explained by the high reactivity of the inventive compounds when compared to prior art precursors. This is illustrated in Table II, which presents the peracid generation of inventive embodiments (1) and (2) in comparison with peracid generation of prior art compound (3) at 5° C.

TABLE II

Comparative Peracid Generation at 5° C.*

| | A.O. (ppm) Generated by Precursor at 5° C. | | |
|---|---|---|---|
| Time (min) | Inventive Embodiment (1) | Inventive Embodiment (2) | Prior Art (3) |
| 1 | 9.4 | 9.2 | 4.7 |
| 2 | 10.0 | 9.7 | 6.0 |
| 3 | 10.3 | 9.9 | 6.7 |
| 6 | 10.7 | 10.3 | 7.7 |
| 8 | 10.8 | 10.6 | 8.0 |
| 10 | 10.7 | 10.6 | 8.2 |

*$[H_2O_2]$:[precursor] = 2:1
[precursor] = $8.75 \times 10^{-4}$M
pH = 10.0 (.02M $CO_3^{=}$ buffer)

Figure 4:
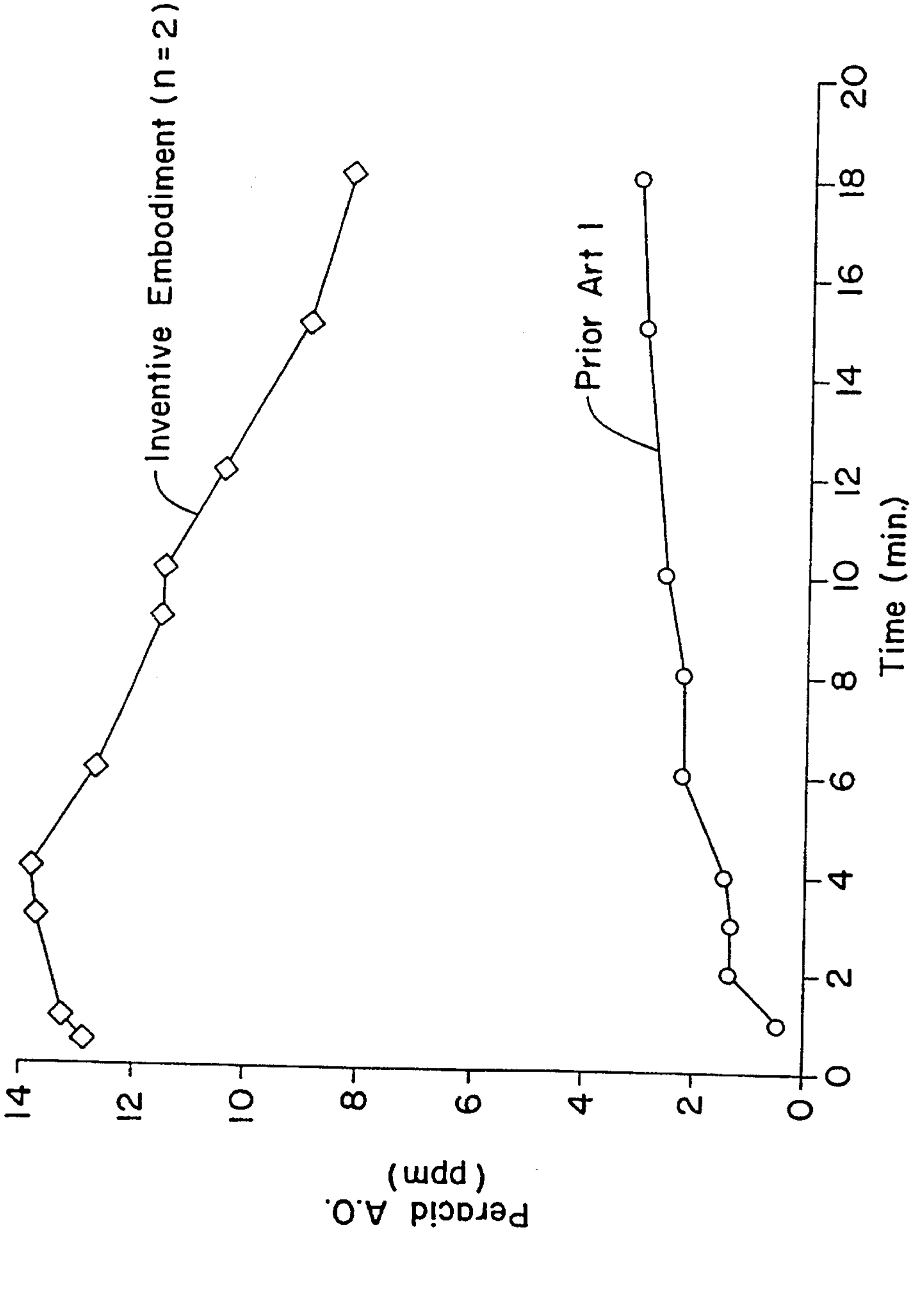
FIG. 4 graphically illustrates the perhydrolysis of a precursor embodiment of the invention as a function of time and, for comparison, the perhydrolysis of one prior art compound (i.e., prior art compound (1)) illustrated in FIG. 2; and, FIG. 5 graphically illustrates the perhydrolysis of a precursor embodiment of the invention as a function of time and, for comparison, the perhydrolysis of another prior art compound (prior art compound (2)) illustrated in FIG. 2.

FIG. 4 illustrates another comparison between the prior art (1) compound discussed for FIG. 2 (where n=2) and the inventive compound OOAOAPS (where n=2). Thus, perhydrolysis % yield over 14 minutes at pH 10.5 and 25° C. is illustrated, where $H_2O_2$ and tested compounds were in a 2:1 mole ratio. As can be seen, the inventive OOAOAPS provided significantly greater yield of peracid over the 14 minute period (representing the usual maximum wash cycle) than did the prior art (1) compound. This indicates that peracid precursors of the invention achieve and maintain superior levels of bleaching capacity over a typical wash cycle.

Figure 5:
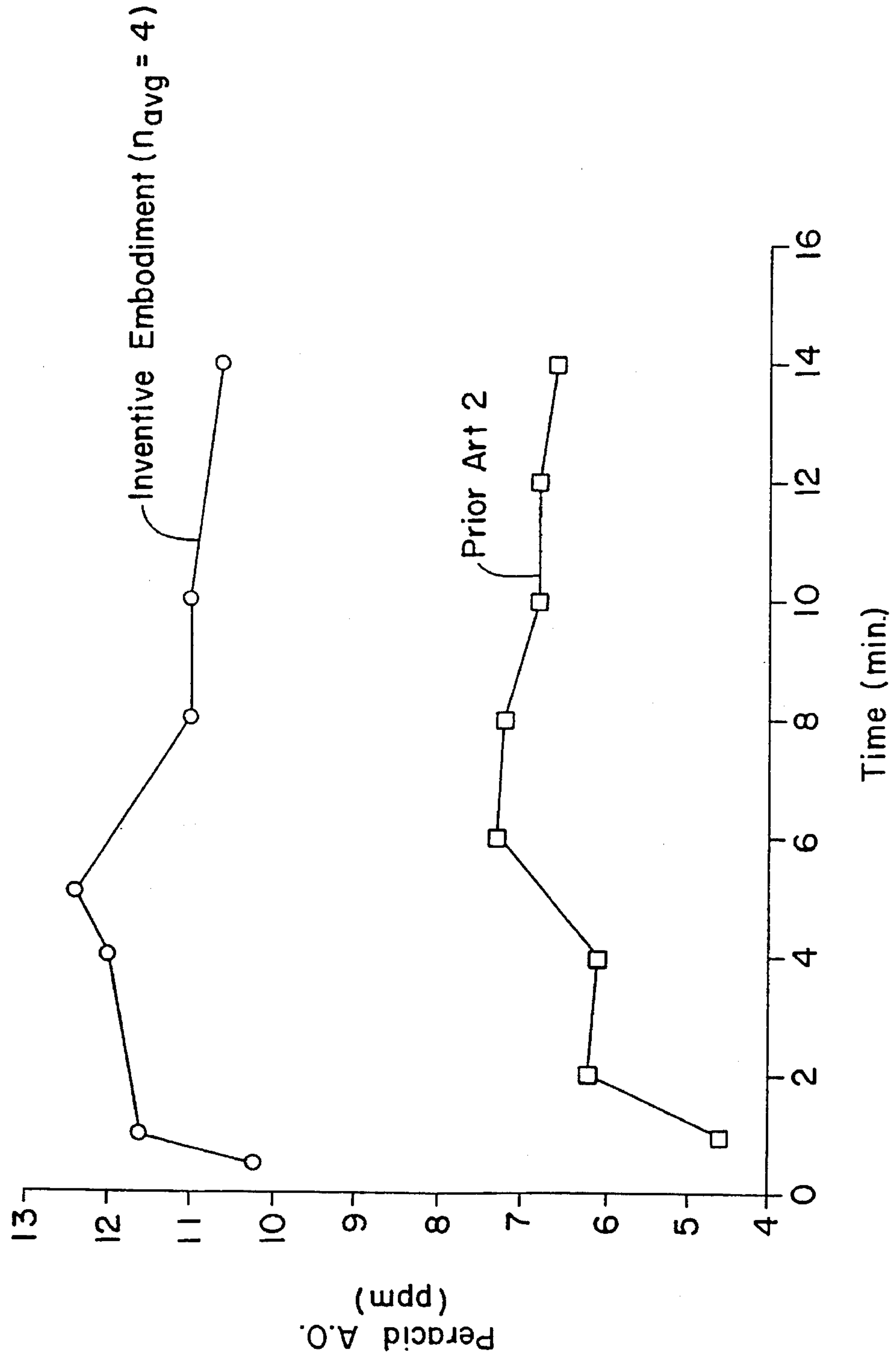

FIG. 5 is similar to FIG. 4, but illustrates a comparison between the inventive precursor OOPOAPS (where n averages 4) and the prior art (2) compound and was conducted at pH 10. Again, the inventive precursor provided significantly greater yield of peracid over the 14 minute period. Both FIGS. 4 and 5 were conducted with a precursor concentration of $8.75 \times 10^{-4}$M (i.e., 14 ppm A.O. theoretical).

Preparation of particularly preferred embodiments of the invention and additional experimental details will be described in the Experimental section of this specification, following a brief review of definitions and a detailed description of suitable leaving groups and delivery systems for precursors of the invention.

By peracid precursors are meant reactive esters which have a leaving group substituent. During perhydrolysis the leaving group cleaves off at the acyl portion of the ester.

By perhydrolysis is meant the reaction that occurs when a peracid precursor is combined in a reaction medium (aqueous solution) with an effective amount of a source of hydrogen peroxide.

As may be seen, the leaving group is a substituent which is attached via an oxygen bond to the acyl portion of the ester and which can be replaced by a perhydroxide anion (—OOH) during perhydrolysis.

In the Formula I structure of the invention, R is defined as being $C_{1-20}$ linear or branched alkyl, alkoxylated alkyl, cycloalkyl, aryl, substituted aryl or alkylaryl.

It is preferred that R is $C_{1-20}$ alkyl or alkoxylated alkyl. More preferably, R is $C_{1-14}$, and mixtures thereof. R can also be mono-unsaturated or polyunsaturated. If alkoxylated, ethoxy and propoxy (branched or unbranched) groups are preferred, and can be present per mole of ester from 1–30 ethoxy or propoxy groups, and mixtures thereof.

It is especially described for R to be from 4 to 17, most preferably 6 to 12, carbons in the alkyl chain. Such alkyl groups provide surface activity and are desirable when the precursor is used to form surface active peracids for oxidizing soils and stains affixed to fabric surfaces at relatively low temperatures.

It is further highly preferred for R to be aryl and $C_{1-20}$ alkylaryl. A different type of bleaching compound results when aromatic groups are introduced onto the ester.

Alkyl or alkanoyl groups are generally introduced onto the ester via an acid chloride synthesis discussed further below, although acid anhydrides may also be used. Fatty acid chlorides such as hexanoyl chloride, heptanoyl chloride, octanoyl chloride, nonanoyl chloride, decanoyl chloride and the like provide this alkyl moiety. Aromatic groups can be introduced via aromatic acid chlorides (e.g., benzoyl chloride) or aromatic anhydrides (e.g., benzoic acid anhydride).

R' and R" are independently H, $C_{1-20}$ alkyl, aryl, $C_{1-20}$ alkylaryl, substituted aryl, and $NR_3^{\alpha+}$, wherein $R^{\alpha}$ is $C_{1-30}$ alkyl. When R' and R" are both alkyl, aryl, alkylaryl, substituted alkyl or mixtures thereof, preferably the total number of carbons of R'+R" does not exceed about 20, more preferably does not exceed about 18. Alkyls of about 1-4 are preferred. If substituted aryl, OH—, $SO_3$—, and $CO_2$—; $NR_3^{\alpha+}$ ($R^{\alpha}$ is $C_{1-30}$ carbons, and preferably, two of $R^{\alpha}$ is a long chain alkyl ($C_{6-24}$). Appropriate positive counterions include $Na^+$, $K^+$, etc. and appropriate negative counterions include halogen (e.g., Cl—), OH— and methosulfate. It is preferred that at least one of R' and R" be H, and most preferably, both (thus forming methylene).

The leaving group, as discussed above, is capable of being displaced by perhydroxide anion in aqueous medium.

The preferred leaving groups include: phenol derivatives, halides, oxynitrogen leaving groups, and carboxylic acid (from a mixed anhydride). Each of these preferred leaving groups will now be more specifically described.

Phenol Derivatives

The phenol derivatives can be generically defined as:

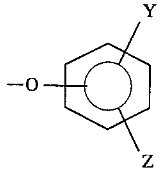

wherein Y and Z are, individually H, $SO_3M$, $CO_2M$, $SO_4M$, OH, halo substituent, —$OR^2$, $R^3$, $NR_3{}^4X$, and mixtures thereof, wherein M is an alkali metal or alkaline earth counterion, $R^2$ of the $OR^2$ substituent is $C_{1-20}$ alkyl, $R^3$ is $C_{1-6}$ alkyl, $R^4$ of the $NR_3{}^4$ substituent $C_{1-30}$ alkyl X is a counterion, and Y and Z can be the same or different.

The alkali metal counterions to sulfonate, sulfate or carboxy (all of which are solubilizing groups) include $K^+$, $Li^+$ and most preferably, $Na^+$. The alkaline earth counterions include $Sr^{++}$, $Ca^{++}$, and most preferably, $Mg^{++}$. Ammonium ($NH_4{}^+$) and other positively charged counterions may also be suitable. The halo substituent can be F, Br or most preferably, Cl. When —$OR^2$, alkoxy, is the substituent on the phenyl ring, $R^2$ is $C_{1-20}$, and the criteria defined for R on the acyl group apply. When $R^3$ is the substituent on the phenyl ring, it is a $C_{1-10}$ alkyl, with preference given to methyl, ethyl, N- and isopropyl, N-, sec- and tertbutyl, which is especially preferred. When —$NR_3{}^4X$ (i.e. quaternary ammonium) is the substituent, it is preferred that two of $R^4$ be short chain alkyls ($C_{1-4}$, most preferably, methyl) and one of the $R^4$ alkyls be longer chain alkyl (e.g., $C_{8-30}$), with X, a negative counterion, preferably selected from halogen (Cl—, F—, Br—, I—), $CH_3SO_4$— (methosulfate), $NO_3$—, or OH—.

Especially preferred are phenol sulfonate leaving groups. A preferred synthesis of phenol sulfonate esters which could be adapted for use herein is disclosed in U.S. Pat. No. 4,735,740, inventor Alfred G. Zielske, entitled "Diperoxyacid Precursors and Method" issued Apr. 5, 1988. Preferred phenol derivatives are:

—O-Ø-$SO_3M$ (especially sodium p-phenyl sulfonate)

—O-Ø-OH (p-, o- or m-dihydroxybenzene)

—O-Ø-$C(CH_3)_3$ (t-butyl phenol)

—O-Ø-$CO_2H$ (4-oxy-Benzoic Acid)

Halides

The halide leaving groups are quite reactive and actually are directly obtained as the intermediates in the synthesis of the phenyl sulfonate and t-butylphenol esters. While halides include Br and F, Cl is most preferred.

Oxynitrogen

The oxynitrogen leaving groups are especially preferred. In the co-pending application entitled "Acyloxynitrogen Peracid Precursors", inventor Alfred G. Zielske, commonly assigned to The Clorox Company, Ser. No. 928,065, filed Nov. 6, 1986, incorporated herein by reference, a detailed description of the synthesis of these leaving groups is disclosed. The oxynitrogen leaving groups are generally disclosed as —$ONR^6$, wherein $R^6$ comprises at least one carbon which is singly or doubly bonded directed to N. Thus, —$ONR^6$ is more specifically defined as:

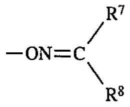

Oxime

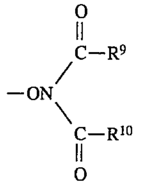

or

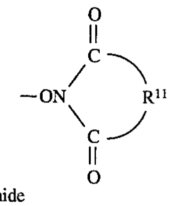

Hydroxyimide

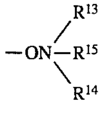

or

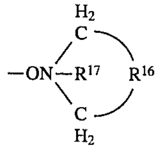

Amine Oxide

Oxime leaving groups have the structure

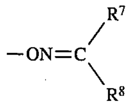

wherein $R^7$ and $R^8$ are individually H, $C_{1-20}$ alkyl, (which can be cycloalkyl, straight or branched chain), aryl, or alkylaryl and at least one of $R^7$ and $R^8$ is not H. Preferably $R^7$ and $R^8$ are the same or different, and range from $C_{1-6}$. Oximes are generally derived from the reaction of hydroxylamine with either aldehydes or ketones.

Examples of oxime leaving groups are: oximes of aldehydes (aldoximes), e.g., acetaldoxime, benzaldoxime, propionaldoxime, butylaldoxime, heptaldoxime, hexaldoxime, phenylacetaldoxime, p-tolualdoxime anisaldoxime, caproaldoxime, valeraldoxime and p-nitrobenzaldoxime; and oximes of ketones (ketoximes), e.g., acetone oxime (2-propanone oxime), methyl ethyl ketoxime (2-butanone oxime), 2-pentanone oxime, 2-hexanone oxime, 3-hexanone oxime, cyclohexanone oxime, acetophenone oxime, benzophenone oxime and cyclopentanone oxime.

Particularly preferred oxime leaving groups are:

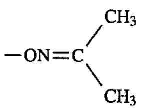

Acetone Oxime

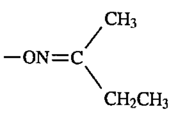

Methylethyl Ketoxime

Hydroxyimide leaving groups comprise:

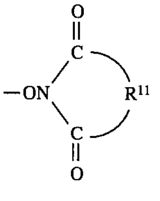

or

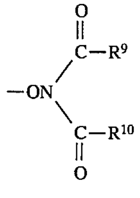

wherein $R^9$ and $R^{10}$ can be the same or different, and are preferably straight chain or branched $C_{1-20}$ alkyl, aryl, alkylaryl or mixtures thereof. If alkyl, $R^9$ and $R^{10}$ can be partially unsaturated. It is especially preferred that $R^9$ and $R^{10}$ are straight or branched chain $C_{1-6}$ alkyl, which can be the same or different. $R^{11}$ is preferably $C_{1-20}$ alkyl, aryl or alkylaryl, and completes a heterocycle. For example, a preferred structure is

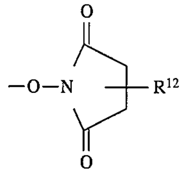

wherein $R^{12}$ can be an aromatic ring fused to the heterocycle, or $C_{1-6}$ alkyl (which itself could be substituted with water solubilizing groups, such as EO, PO, $CO_2$— and $SO_3$—).

The esters of imides can be prepared as described in *Greene, Protective Groups in Organic Synthesis,* p. 183, and are generally the reaction products of acid chlorides and hydroxymides.

Examples of N-hydroxyimides which will provide the hydroxyimide leaving groups of the invention include: N-hydroxysuccinimide, N-hydroxyphthalimide, N-hydroxyglutarimide, N-hydroxynaphthalimide, N-hydroxymaleimide, N-hydroxydiacetylimide and N-hydroxydipropionylimide.

Especially preferred examples of hydroxyimide leaving groups are:

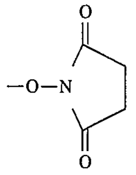

Oxysuccinimide

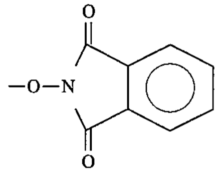

Oxyphthalimide

Amine oxide leaving groups comprise:

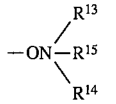

or

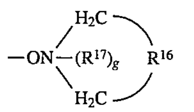

In the first preferred structure for amine oxides, $R^{13}$ and $R^{14}$ can be the same or different, and are preferably $C_{1-20}$ straight or branched chain alkyl, aryl, alkylaryl or mixtures thereof. If alkyl, the substituent could be partially unsaturated. Preferably, $R^{13}$ and $R^{14}$ are $C_{1-4}$ alkyls and can be the same or different. $R^{15}$ is preferably $C_{1-30}$ alkyl, aryl, alkylaryl and mixtures thereof. This $R^{15}$ substituent could also be partially unsaturated. It is more preferred that $R^{13}$ and $R^{14}$ are relatively short chain alkyl groups ($CH_3$ or $CH_2CH_2$) and $R^{15}$ is preferably $C_{1-20}$ alkyl, forming together a tertiary amine oxide.

Further, in the second preferred amine oxide structure, $R^{16}$ can be $C_{1-20}$ alkyl, aryl or alkylaryl, and completes a heterocycle. $R^{16}$ preferably completes an aromatic heterocycle of 5 carbon atoms and can be $C_{1-6}$ alkyl or aryl substituted. $R^{17}$ is preferably nothing, $C_{1-30}$ alkyl, aryl, alkylaryl or mixtures thereof, with g=0 or 1. $R^{17}$ is more preferably $C_{1-20}$ alkyl if $R^{16}$ completes an aliphatic heterocycle. If $R^{16}$ completes an aromatic heterocycle, $R^{17}$ is nothing.

Examples of amine oxides suitable for use as leaving groups herein can be derived from: pyridine N-oxide, trimethylamine N-oxide, 4-phenyl pyridine N-oxide, decyldimethylamine N-oxide, dodecyldimethylamine N-oxide, tetradecyldimethylamine N-oxide, hexadecyldimethylamine oxide, octyldimethylamine N-oxide, di(decyl)methylamine N-oxide, di(dodecyl)methylamine N-oxide, di(tetradecyl)methylamine N-oxide, 4-picoline N-oxide, 3-picoline N-oxide and 2-picoline N-oxide.

Especially preferred amine oxide leaving groups include:

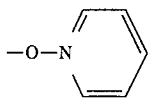

Pyridinium N-oxide

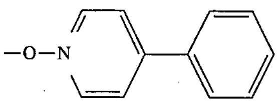

Phenylpyridinium N-Oxide

Carboxylic Acids from Mixed Anhydrides

Carboxylic acid leaving groups have the structure

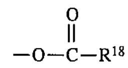

wherein $R^{18}$ is $C_{1-10}$ alkyl, preferably $C_{1-4}$ alkyl, most preferably either $CH_3$ or $CH_2CH_3$ and mixtures thereof.

When $R^{18}$ is $C_1$ and above, it is believed that the leaving groups will form carboxylic acids upon perhydrolytic conditions. Thus, when $R^{18}$ is $CH_3$, acetic acid would be the leaving group; when $CH_2CH_3$, propionic acid would the leaving group, and so on. However, this is a possible explanation for what may be a very complicated reaction.

Examples of mixed anhydride esters include alkanoyloxyacetyl-oxyacetic or alkanoyl-poly[oxyacetyl]-oxyacetic/acetic or propionic mixed anhydride.

Delivery Systems

The precursors can be incorporated into a liquid or solid matrix for use in liquid or solid detergent bleaches by dissolving into an appropriate solvent or surfactant or by dispersing onto a substrate material, such as an inert salt (e.g., NaCl, $Na_2SO_4$) or other solid substrate, such as zeolites, sodium borate, or molecular sieves. Examples of appropriate solvents include acetone, non-nucleophilic alcohols, ethers or hydrocarbons. Other more water-dispersible or -miscible solvents may be considered. As an example of affixation to a substrate material, the precursors of the present invention could be incorporated onto a non-particulate substrate such as disclosed in published European patent application EP No. 98 129.

While substituting solubilizing groups may improve the solubility and enhance the reactivity of these precursors, an alternate mode and preferred embodiment is to combine the precursors with a surfactant.

For example, the inventive precursors with oxynitrogen leaving groups are apparently not as soluble in aqueous media as compared to phenyl sulfonates. Other precursors may be similarly somewhat less soluble than phenyl sulfonate esters. Thus, a preferred embodiment of the invention is to combine the precursors with a surfactant. It is particularly preferred to coat these precursors with a nonionic or anionic surfactant that is solid at room temperature and melts at above about 40° C. A melt of surfactant may be simply admixed with peracid precursor, cooled and chopped into granules. Exemplary surfactants for such use are illustrated in Table I below.

TABLE I

| Commercial Name | m.p. | Type | Supplier |
|---|---|---|---|
| Pluronic F-98 | 55° C. | Nonionic | BASF Wyandotte |
| Neodol 25-30 | 47° C. | Nonionic | Shell Chemical |
| Neodol 25-60 | 53° C. | Nonionic | Shell Chemical |
| Tergitol-S-30 | 41° C. | Nonionic | Union Carbide |
| Tergitol-S-40 | 45° C. | Nonionic | Union Carbide |
| Pluronic 10R8 | 46° C. | Nonionic | BASF Wyandotte |
| Pluronic 17R8 | 53° C. | Nonionic | BASF Wyandotte |
| Tetronic 90R8 | 47° C. | Nonionic | BASF Wyandotte |
| Amidox C5 | 55° C. | Nonionic | Stepan |

The precursors, whether coated with the surfactants or not so coated, could also be admixed with other surfactants to provide either bleach additive or detergent compositions.

Particularly effective surfactants appear to be non-ionic surfactants. Preferred surfactants include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Anionic surfactants may also be suitable. Examples of such anionic surfactants may include the ammonium, substituted ammonium (e.g., mono- di-, and triethanolammonium), alkali metal and alkaline earth metal salts of $C_{6-20}$ fatty acids and rosin acids, linear and branched alkyl benzene sulfonates, alkyl sulfates, alkyl ether sulfates, alkane sulfonates, alpha olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

As mentioned above, other common detergent adjuncts may be added if a bleach or detergent bleach product is desired. If, for example, a dry bleach composition is desired, the following ranges (weight %) appear practicable:

| | |
|---|---|
| 0.5–50.0% | Hydrogen Peroxide Source |
| 0.05–25.0% | Precursor |
| 1.0–50.0% | Surfactant |
| 1.0–50.0% | Buffer |
| 5.0–99.9% | Filler, stabilizers, dyes, Fragrances, brighteners, etc. |

The hydrogen peroxide source may be selected from the alkali metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates. In liquid applications, liquid hydrogen peroxide solutions are preferred, but the precursor may need to be kept separate therefrom prior to combination in aqueous solution to prevent premature decomposition.

The range of peroxide to peracid precursor is preferably determined as a molar ratio of peroxide to precursor. Thus, the range of peroxide to each precursor is a molar ratio of from about 0.1:1 to 10:1, more preferably about 1:1 to 10:1 and most preferably about 2:1 to 8:1. This peracid precursor/peroxide composition should provide about 0.5 to 100 ppm A.O., more preferably about 1 to 50 ppm peracid A.O. (active oxygen), and most preferably about 1 to 20 ppm peracid A.O., in aqueous media.

An example of a practical execution of a liquid delivery system is to dispense separately metered amounts of the precursor (in some non-reactive fluid medium) and liquid hydrogen peroxide in a container such as described in Beacham et al., U.S. Pat. No. 4,585,150, issued Apr. 29, 1986.

The buffer may be selected from sodium carbonate, sodium bicarbonate, sodium borate, sodium silicate, phosphoric acid salts, and other alkali metal/alkaline earth metal salts known to those skilled in the art. Organic buffers, such as succinates, maleates and acetates may also be suitable for use. It appears preferable to have sufficient buffer to attain an alkaline pH. It is especially advantageous to have an amount of buffer sufficient to maintain a pH in the range of about 8.5 to about 10.5.

The filler material (which may actually constitute the major constituent by weight of the detergent bleach) is usually sodium sulfate. Sodium chloride is another potential filler. Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion. Brighteners, such as stilbene, styrene and styrylnaphthalene brighteners (fluorescent whitening agents), may be included. Fragrances used for aesthetic purposes are commercially available from Norda, International Flavors and Fragrances and Givaudon. Stabilizers include hydrated salts, such as magnesium sulfate, and boric acid.

EXPERIMENTAL

Example I describes the synthesis of sodium-p-(n-octanoyl-di-[oxyacetyl]-oxy)-benzene sulfonate [OOAOAPS]. Example II describes the synthesis of sodium-p-(n-octanoyl-poly[oxyacetyl]-oxy)-benzene sulfonate (with the average value of n=4). Example III describes another synthesis where an admixture of polyglycolate precursors are formed but with a lower degree of oligomerization than in Example II. Example IV describes the synthesis of another precursor embodiment of the invention, where the leaving group is an oxime. Example V describes the procedure for the crystal violet diagnostic stain removal determinations illustrated by FIGS. 2 and 3 with the compounds prepared from Examples I and II.

EXAMPLE I

Synthesis of Benzyl Glycolate

A 500 ml round bottom flask, equipped with a Dean-Stark apparatus and heated by an oil bath, was charged with 25 g (0.329 mole) glycolic acid, which had been recrystallized from ethyl acetate, 40 g (0.378 mole) benzyl alcohol, 150 ml benzene and 15 drops concentrated sulfuric acid. This mixture was heated to reflux while stirring with a magnetic stir bar, and water was removed by azeotrope. After two hours, 5.9 ml (approx. 0.328 mole) of water had been removed, and the reaction was cooled to room temperature. The reaction was diluted with 250 ml of diethyl ether and extracted with: 3×200 ml 4% aqueous $NaHCO_3$ saturated with NaCl. The organic layer was dried over $MgSO_4$, filtered, and rotary evaporated to an oil (wt=50 g), which was approximately 64% product by G.C. This material was chromatographed on silica gel using ethyl acetate/hexane as mobil phase, yielding 20 g of product that was 95% in purity by G.C. $^1H$ NMR confirmed the structure to be that of benzyl glycolate (t at 3.2 ppm, 1H; d at 4.0 ppm, 2H; s at 5.0 ppm, 2H; and m at 7.2 ppm, 5 H. All shifts downfield from TMS). IR shows $V_{—OH}$ at 3420 $cm^{-1}$ and $V_{—C=O}$ at 1748 $cm^{-1}$.

Synthesis of Benzyl (octanoyl-oxyacetyl-oxyacetate)

1) Octanoyl-oxyacetyl Chloride: 9 7 g (0.048 mole) octanoyl-oxyacetic acid was suspended in 50 ml hexane at room temperature, and 5.4 ml oxalyl chloride (approx. 0.05 mole) was added in one portion with stirring. A $CaSO_4$ drying tube was attached, and the reaction was stirred overnight at room temperature. The clear reaction solution was then gradually warmed to 60° C. in an oil bath. A distillation head and condenser was attached, and the excess oxalyl chloride was distilled off along with the hexane solvent. This left 10.6 g of light straw colored oil that had no $V_{—OH}$ and strong $V_{—C=O}$ at 1812 cm $^{-1}$ and 1755 $cm^{-1}$.

2) Benzyl (octanoyl-oxyacetyl-oxyacetate): A round bottom flask was charged with 8.0 g (0.048 mole) benzyl glycolate, 8.0 g (0.101 mole) pyridine, and 30 ml anhydrous diethyl ether. This was cooled in an ice-water bath while stirring with a magnetic stirring bar. An addition funnel containing the acid chloride from reaction 1 above in 30 ml ether was attached, and this was added dropwise to the alcohol/pyridine solution (a white ppt. formed upon addition) over 30 minutes. The reaction was then stirred for 1 and ½ hours at room temperature, filtered and extracted with: 2×200 ml 4% aqueous HCl, 4×200 ml 10% aqueous $NaHCO_3$, and 1×200 ml saturated NaCl. The ether layer was dried over $MgSO_4$, filtered and rotary evaporated to an oil. Vacuum drying left 14.9 g of material. This was chromatographed on 150 g of flash grade silica gel with 10% ethyl ether in hexane (vol/vol). The combined product fractions yielded 11 g of 94% (G.C.) product. IR shows no $V_{—OH}$ and a strong, broad $V_{—C=O}$ centered at 1760 $cm^{-1}$, with aromatic C—H stretch at 3040 and 3060 $cm^{-1}$ and aliphatic C—H stretches at 2955, 2925 and 2860 $cm^{-1}$. TLC (20% ethyl ether in hexane on silica GF) indicates one component ($I_2$ stain) with an $R_f$ of 0.38.

Hydrogenolysis of Benzyl (octanoyl-oxyacetyl-oxy-acetate)

1.3 g 10% Pd/C was weighed into a 500 ml parr hydrogenation flask. 9.96 g (0.028 mole) Benzyl(Octanoyl-oxyacetyl-oxyacetate) dissolved in 100 ml ethyl acetate was added to the catalyst under a nitrogen blanket. The flask was attached to the hydrogenation apparatus, and after a series of evacuations and fillings with hydrogen, the mixture was shaken for 6 hours under hydrogen pressure ($P_0$=14.9 psig, $P_{6hrs}$=12.0 psig). The reaction was filtered through celite under a nitrogen blanket, and solvent removed by rotary evaporation. Vacuum drying left 7.4 g of an oil which crystallized upon standing. G.C. of the TMS ester of this material indicates it to be approximately 84% in purity. IR shows an acid $V_{—OH}$ at 3400–2500 $cm^{-1}$ and a broad $V_{—C=O}$ centered at 1740–1780 $cm^{-1}$. $^{13}C$ NMR exhibits three carbonyl resonances at 167.4, 171.9 and 173.2 ppm downfield from TMS, as well as the two glycolic methylenes at 60.1 and 60.5 ppm (spectrum run in $CDCl_3$).

Synthesis of Octanoyl-oxyacetyl-oxyacetyl Chloride 5.6 g (0.022 mole) octanoyl-oxyacetyl-oxyacetic acid, 50 ml hexane were placed in a 250 ml round bottom flask. 2.9 ml (0.03 mole) oxalyl chloride was added in one portion and the reaction stirred at room temperature for 6 hours. The reaction was then heated to 80° C., a distillation head attached with condenser and receiver, and the excess oxalyl chloride and solvent removed at reduced pressure. There remained 4.5 g of light yellow oil. IR spectrum reveals no free —OH and a broad $V_{—C=O}$ absorbance, with maxima at 1815, 1780 and 1755 $cm^{-1}$.

Synthesis of Sodium-p-(n-octanoyl -di-[oxyacetyl]-oxy)-Benzene Sulfonate

A 250 ml round bottom flask with magnetic stirrer was charged with 4.5 g n-octanoyl-oxyacetyl-oxyacetyl chloride (approx. 0.022 mole), 4.8 g (0.025 mole) anhydrous sodium-p-phenol-sulfonate, and 75 ml DMF. The reaction was chilled with stirring in an ice-water bath, and 3.5 g (0.35 mole) triethylamine was added dropwise over 20 minutes. The reaction thickened upon the amine addition, as a precipitate formed. After stirring an additional 1 hour the slurry was diluted with 200 ml diethyl ether and filtered on a paper filter overnight. There remained 9 g of waxy solid on the filter paper. Two recrystallizations form 50/50 methanol/water/water yielded 3.8 g of shiny light brown flakes that were determined by HPLC, saponification and $^{13}C$ NMR to be the desired phenol sulfonate ester n 97wt. purity. (NMR: three carbonyl resonances at 173, 168 and 166.5 ppm in 1:1:1 ratio; four aromatic carbon resonances at 121, 127.5, 146 and 150 ppm in 2:2:1:1: ratio; two glycolate ethylene resonances at 60.5 and 62 ppm in 1:1 ratio; and the expected $C_7H_{15}$— alkyl chain resonances (all downfield from TMS)).

EXAMPLE II

Glycolic Acid Condensation 305 g (2.8 mole) of 70% aqueous glycolic acid and 150 ml benzene were combined in a round bottom flask equipped with a magnetic stirrer, oil bath heater, and Dean-Stark apparatus. The resulting two phase mixture was heated to reflux and water removed by azeotropic distillation. After 20 hours of heating with the oil bath at 120° C. a total of 120 ml of water had been removed (this amounts to approximately a 57 mole % excess beyond the water of solvation) the solvent was distilled off, and the reaction cooled to room temperature and dried in vacuo. To the pasty residue was added 250 ml of DMF, and this was stirred with warming for 3 hours, cooled and filtered on a paper filter. The solid filtrate was extracted with two portions of acetone, filtered and these were combined with the DMF solution. Solvent removal by rotary evaporation and drying in vacuo left 150 g of soluble glycolic acid n-mers, with n=1 to 11 (determined by LC, GC of TMS esters, and MS), and a maximum in the n=3 to 5 domain. This material was used "as is" for the subsequent acylation reaction.

Acylation of Glycolic Acid Oligomers

A 500 ml round bottom flask was charged with 31 g (approx. 0.124 mole for $n_{avg.}$=4) of n-meric glycolic acid, and 100 ml DMF. A clear solution was obtained upon warming on an oil bath with stirring by magnetic stir bar. 25 g (0.34 mole) $Li_2CO_3$ and 20 g (0.17 mole) $MgSO_4$ were then added and thoroughly dispersed by stirring. An addition funnel containing 75 ml (0.44 mole) octanoyl chloride was attached and the contents added dropwise over 3 hours. A moderate level of $CO_2$ evolution was observed through a bubbler during the addition. The reaction was then stirred 56 hours, at which time 5.6 g (0.076 mole) more $Li_2CO_3$ was added. While stirring for 2 hours more, little gas evolution was seen. 20 ml methanol was added to quench the residual acid chloride, and after 1 hour more stirring the reaction was diluted with 200 ml $CHCl_3$ and filtered to remove salts. Solvent was removed by rotary evaporation and the oily residue extracted with 3×250 ml hexane leaving a gummy residue weighing 67 g after drying in vacuo. 39.3 g of this material was dissolved in 500 ml of 0.5N $NaHCO_3$. This was then acidified to pH 2 with aqueous HCl and the resulting precipitate isolated by filtration, redissolved in $CH_3CN$, dried over $MgSO_4$, filtered and rotary evaporated to a waxy material. Vacuum drying left 8.4 g of material that was clean by HPLC and $^{13}C$ NMR, giving a distribution of acylated glycolic acid n-mers with n=1 to 10 and an $n_{avg.}$=4.0 to 4.5 on a mole basis.

Octanoyl-poly[oxyacetyl]-oxyacetyl chloride

In a 250 ml round bottom flask 5.0 g (approx. 0.013 mole for $n_{avg.}$=4) of $C_8$ acylated glycolic acid n-mers was dissolved in 25 ml $CHCl_3$, followed by the addition of 2.0 ml oxalyl chloride. This was stirred under a $CaSO_4$ drying tube overnight at room temperature. The reaction was gradually heated to 70° C. on an oil bath and a distillation apparatus was attached. The excess oxalyl chloride and solvent were removed by distillation leaving 2.5 g of a light yellow colored oil. IR of this material shows no free —OH and a broad $V_{—C=O}$ with a distinct peak at 1810 $cm^{-1}$.

Sodium-p-(octanoyl-poly[oxyacetyl]-oxy)-Benzene Sulfonate.

To 5.2 g (0.013 mole) octanoyl-poly(oxyacetyl)-oxyacetyl chloride ($n_{avg.}$=4) in a 250 ml round bottom flask was added 3.6 g (0.018 mole) anhydrous sodium-p-phenol sulfonate and 40 ml anhydrous ethylene glycol-dimethyl ether (glyme). This slurry was stirred with a magnetic stir bar and chilled in an ice water bath while 2.0 ml triethylamine (TEA) in 8.0 ml glyme was added dropwise with stirring over 10 minutes. The resultant thickened slurry was stirred at 4° C. for 15 minutes, then at room temperature for 45 minutes, diluted with 300 ml diethyl ether and filtered on a paper filter. Vacuum drying of the filtrate left 10.5 g of tan waxy material. Recrystallization from 25 ml of 70/30 (vol/vol) IPA:water yielded 3.4 g of product that was 85–90% pure by HPLC. A second recrystallization provided $97^{+}$% material. $^{13}C$ NMR confirmed the proposed structure (in $d^6$-DMSO: multiple C═O resonances at 166.0 to 167.3 ppm and a single resonance at 172.3 ppm; aromatic resonances at 149.7, 146.1, 127.0, and 120.7 ppm; multiple glycolate methylene resonances at 62.0 to 60.2 ppm; and the characteristic C-7 alkyl chain resonances, with all shifts downfield from TMS), and HPLC showed it to be a mixture of the desired esters of the acylated glycolic n-mers, with n=2 to 10 and a maximum in the distribution at n=3 to 5 ($n_{avg.}$=4–4.5 by NMR and HPLC).

EXAMPLE III

Glycolic Acid Condensation 150 g (1.38 moles) of 70% aqueous glycolic acid and 150 ml benzene were combined in a 500 ml round bottom flask, equipped with a hot oil bath, a magnetic stirrer, and a Dean-Stark apparatus. This mixture was heated to reflux and water removed by azeotropic distillation. After 10 hours, 54 g of water had been removed, and the solvent was stripped off at reduced pressure, leaving behind 97 g of a tan liquid which crystallized upon cooling. G.C. analysis of the TMS esters of this material showed it to be a mixture of glycolic acid n-mers in a ratio of 47 (n=1): 32 (n=2): 16 (n=3): 5 (n=4). The average n value of this mixture was calculated to be 1.8.

The material so formed in Example III is then used "as is" for the subsequent acylation reaction as described in Example II, and illustrated by Reaction Scheme III. This procedure is a particularly preferred method of preparing an admixture of monoglycolate and polyglycolate precursors of the invention.

EXAMPLE IV

Methyl-Ethyl-Ketoxime Ester of n-Octanoylpoly[oxyacetyl]-oxyacetic Acid

The methyl-ethyl ketoxime ester of the $C_8$-acylpoly glycolic acid ($n_{avg}$=4) was prepared as follows. 4 g (0.046 mole) methyl ethyl ketoxime, 5 ml (0.06 mole) pyridine, and 50 ml anhydrous THF were placed in a 500 ml round bottom flask. This solution was chilled in an ice water bath while stirring. An additional funnel containing 12 g (0.027 mole) n-octanoyl-poly[oxyacetyl]-oxyacetyl chloride, prepared as described previously, in 50 ml THF was attached to the reaction vessel, and its contents were added dropwise over 40 minutes to the chilled ketoxime/pyridine solution. After 2 hours of additional stirring at 4° C. the reaction was filtered to remove the precipitated pyridine hydrochloride, and the clear filtrate was diluted with 300 ml diethyl ether. The ether solution was washed with: 2×200 ml 0.5% aqueous HCl, 1×200 ml D.I. water, and 1×200 ml saturated aqueous NaCL. The ether layer was dried over $MgSO_4$, filtered and rotary evaporated to a yellow oil weighing 11.8 g (12.0 g theo.). Purified material was obtained by chromatography on an amino-bonded silica gel column. IR ($V_{C=O}$(s) at 1760 $cm^{-1}$ and no $V_{OH}$ and $^{13}C$ NMR (multiple C═O resonances at 165.6 to 168.5 ppm and at 172.8 ppm, glycolate $CH_2$ resonances at 59.9 to 60.6 ppm) confirmed the structure of this material.

EXAMPLE V

Procedure for Crystal Violet Diagnostic Stain Removal Determination a) Staining of Swatches: 100 2"×2" 100% scoured cotton swatched (Test Fabrics Inc.) were soaked overnight in a solution of 0.125 g crystal violet in 1250 ml deionized water. The swatches were rinsed with water until the rinse was nearly free of dye, and then air dried. The HunterLab colorimeter Y value, from the tristimulus XYZ reading, was then determined for each swatch.

b) Stain Removal Procedure: To a solution of 192 ml pH 10.0, 0.02M carbonate buffer, and 2.53 ml ($2.51\times10^{-4}$ Mole) of 0.1386M $H_2O_2$ in distilled water was added $1.75\times10^{-4}$ Mole of peracid precursor dissolved in 5.0 ml of 70:30/ IPA:water, and timing is begun. At t=30 sec. four stained swatches were added to the solution and stirred at the desired temperature for 13.5 minutes. The swatches are then removed from the perhydrolysis solution and thoroughly rinsed with deionized water. After air drying, the post-treatment HunterLab Y value was determined and % SRY was calculated by the Kubelka-Munk equation.

Although the present invention has been described with reference to specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

It is claimed:

1. A peracid having the structure

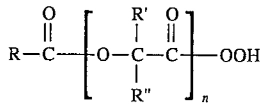

wherein n is an integer from 2 to 4, and R is $C_{1-20}$ linear or branched alkyl, alkoxylated alkyl, cycloalkyl, aryl, alkylaryl, substituted aryl; R' and R" are independently H, $C_{1-20}$ alkyl, aryl, $C_{1-20}$ alkylaryl, substituted aryl, and $NR_3^{\alpha+}$, wherein $R^{\alpha}$ is $C_{1-30}$ alkyl.

2. The peracid as in claim 1 wherein R is $C_{4-17}$ alkyl an R' and R" are both hydrogen or one of R' and R" is hydrogen and the other is methyl.

* * * * *